United States Patent [19]

Grohe et al.

[11] 4,273,573
[45] Jun. 16, 1981

[54] AGENTS FOR REGULATING PLANT GROWTH USING 2-THIAZOLONE-5-CARBOXYLIC ACID COMPOUNDS

[75] Inventors: Klaus Grohe, Odenthal; Klaus Lürssen, Bergisch-Gladbach, both of Fed. Rep. of Germany

[73] Assignee: Bayer Aktiengesellschaft, Leverkusen, Fed. Rep. of Germany

[21] Appl. No.: 26,850

[22] Filed: Apr. 4, 1979

[30] Foreign Application Priority Data

Apr. 27, 1978 [DE] Fed. Rep. of Germany ....... 2818504

[51] Int. Cl.³ ............................................. A01N 43/78
[52] U.S. Cl. ........................................................ 71/90
[58] Field of Search ............................................ 71/90

[56] References Cited

FOREIGN PATENT DOCUMENTS 837517  3/1970  Canada .
1912064  3/1969  Fed. Rep. of Germany .
2253027  5/1974  Fed. Rep. of Germany .
1539784  8/1968  France .

*Primary Examiner*—Catherine L. Mills
*Attorney, Agent, or Firm*—Sprung, Felfe, Horn, Lynch & Kramer

[57] ABSTRACT

Novel method for regulating the growth of plants which method comprises applying to the plants or their habitat, effective amounts of 2-thiazolone-5-carboxylic acid derivatives of the formula

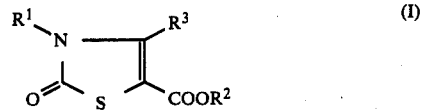

in which
$R^1$ represents hydrogen, alkyl, alkoxyalkyl, alkylmercaptoalkyl, alkyl substituted by a heterocyclic radical, alkyl substituted by alkylcarbonyl or alkyl substituted by arylcarbonyl (which in turn can carry one or more substituents on the aryl part selected independently from halogen, alkyl, halogenoalkyl, alkoxy, alkylthio and nitro), or represents alkenyl, cycloalkyl, optionally substituted aryl, aralkyl which is optionally substituted in the aryl part, or the grouping

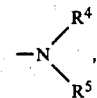

in which
$R^4$ represents hydrogen, alkyl or aryl, and
$R^5$ represents alkyl, alkylcarbonyl, carbalkoxy, alkylsulphonyl or arylsulphonyl or $R^4$ and $R^5$ conjointly with the adjoining nitrogen atom represent a 5-membered to 7-membered heterocyclic ring,
$R^2$ represents hydrogen, alkyl (which is optionally substituted by cycloalkyl, alkoxy, alkylmercapto, phenoxyl, arylthio or cyano), cycloalkyl which is optionally substituted by alkyl, or aralkyl which is optionally substituted, and
$R^3$ represents hydrogen, alkyl, alkoxyalkyl, halogenoalkyl, cycloalkyl, optionally substituted aryl or optionally substituted aralkyl.

31 Claims, No Drawings

AGENTS FOR REGULATING PLANT GROWTH USING 2-THIAZOLONE-5-CARBOXYLIC ACID COMPOUNDS

The present invention relates to methods for regulating plant growth using certain 2-thiazolone-5-carboxylic acid compounds.

Numerous 2-thiazolone-5-carboxylic acid esters are already known, as is their use as fungicides, from DT-OS (German Published Specification) No. 2,253,027.

Furthermore, it is known that succinic acid 2,2-dimethylhydrazide possesses plant growth-regulating properties (see R. Wegler "Chemie der Pflanzenschutz- und Schädlingsbekämpfungsmittel" ("Chemistry of the Plant Protection Agents and Pesticides"), volume 2, page 265). The action of this compound is, however, not always satisfactory, above all if low amounts are used.

Furthermore, it has been disclosed that certain 2-halogenoethyl-trialkylammonium halides possess plant growth-regulating properties (see U.S. Pat. No. 3,156,554). Thus, for example, plant growth can be influenced with the aid of (2-chloroethyl)-trimethylammonium chloride, although the activity of this compound is also not always adequate, above all if low amounts are used.

It has now been found that the 2-thiazolone-5-carboxylic acid derivatives of the general formula

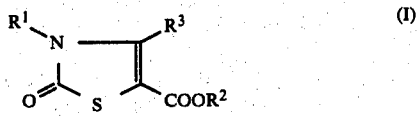

in which

R¹ represents hydrogen, alkyl, alkoxyalkyl, alkylmercaptoalkyl, alkyl substituted by a heterocyclic radical, alkyl substituted by alkylcarbonyl or alkyl substituted by arylcarbonyl (which in turn can carry one or more substituents on the aryl part selected independently from halogen, alkyl, halogenoalkyl, alkoxy, alkylthio and nitro), or represents alkenyl, cycloalkyl, optionally substituted aryl, aralkyl which is optionally substituted in the aryl part, or the grouping

in which

R⁴ represents hydrogen, alkyl or aryl, and

R⁵ represents alkyl, alkylcarbonyl, carbalkoxy, alkylsulphonyl or arylsulphonyl or R⁴ and R⁵ conjointly with the adjoining nitrogen atom represent a 5-membered to 7-membered heterocyclic ring, R² represents hydrogen, alkyl (which is optionally substituted by cycloalkyl, alkoxy, alkylmercapto, phenoxyl, arylthio or cyano), cycloalkyl which is optionally substituted by alkyl, or aralkyl which is optionally substituted, and R³ represents hydrogen, alkyl, alkoxyalkyl, halogenoalkyl, cycloalkyl, optionally substituted aryl or optionally substituted aralkyl possess powerful plant growth-regulating properties.

Accordingly, the present invention provides a method of regulating the growth of plants which comprises applying to the plants, or to a habitat thereof, a compound of the formula (I), alone or in admixture with a diluent or carrier.

Preferably, in formula (I), R¹ represents hydrogen; straight-chain or branched alkyl with 1 to 4 carbon atoms; straight-chain or branched alkoxyalkyl with 1 to 4 carbon atoms in the alkyl group and 1 to 4 carbon atoms in the alkoxy part; straight-chain or branched alkylmercaptoalkyl with 1 to 4 carbon atoms in the alkyl group and 1 to 4 carbon atoms in the alkylmercapto part; straight-chain or branched alkyl with 1 to 4 carbon atoms which is mono-substituted or polysubstituted by saturated or unsaturated heterocyclic radicals with 5 to 7 ring members (preferred heterocyclic radicals being those which contain 1 to 3 hetero-atoms, such as nitrogen and/or oxygen and/or sulphur, examples of such heterocyclic radicals being pyridinyl, piperidinyl, pyrrolidinyl, piperazinyl, pyrazolidinyl, morpholinyl, thiamorpholinyl, thiazolyl, imidazolyl, pyrazolyl, 1,2,4-triazolyl and 1,2,3-triazolyl); straight-chain or branched alkyl with 1 to 4 carbon atoms which is substituted by alkylcarbonyl with up to 5 carbon atoms; straight-chain or branched alkyl with 1 to 4 carbon atoms substituted by phenylcarbonyl or naphthylcarbonyl, in which the phenyl or naphthyl radical can carry one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro; straight-chain or branched alkenyl with 2 to 4 carbon atoms; cycloalkyl with 5 to 7 carbon atoms; aryl with 6 to 10 carbon atoms (for example phenyl) which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro; aralkyl with 6 or 10 carbon atoms in the aryl part and 1 to 4 carbon atoms in the alkyl part (for example benzyl) which optionally carries one or more substituents on the aryl part selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro; or the

group, in which

R⁴ represents hydrogen, straight-chain or branched alkyl with 1 to 6 carbon atoms or aryl with 6 or 10 carbon atoms (for example phenyl), and R⁵ represents straight-chain or branched alkyl with 1 to 6 carbon atoms, alkylcarbonyl with up to 5 carbon atoms, carbalkoxy with up to 5 carbon atoms, alkylsulphonyl with 1 to 4 carbon atoms or arylsulphonyl with 6 or 10 carbon atoms, or R⁴ and R⁵ conjointly with the adjoining nitrogen atom represent a saturated or unsaturated heterocyclic ring with 5 to 7 ring members, in which 1 or 2 carbon atoms in the ring can be replaced by oxygen, sulphur or —SO$_2$— (examples of such heterocyclic radicals bonded via nitrogen being piperidinyl, pyrrolidinyl, morpholinyl, thiomorpholinyl and hexahydroazepinyl), R$^2$ represents hydrogen; alkyl with 1 to 16 carbon atoms which is optionally substituted by cycloalkyl with 5 to 7 carbon atoms, alkoxy with 1 to 4 carbon atoms, alkylmercapto with 1 to 4 carbon atoms, phenoxy, phenylthio or cyano; cycloalkyl with 5 to 7 carbon atoms which is optionally substituted by alkyl with 1 to 4 carbon atoms; or aralkyl with 6 or 10 carbon atoms in the aryl part and 1 to 4 carbon atoms in the alkyl part which optionally carries one or more substituents on the aryl part selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro, and R$^3$ represents hydrogen; straight-chain or branched alkyl with 1 to 4 carbon atoms; straight-chain or branched alkoxyalkyl with 1 to 4 carbon atoms in the alkyl part and 1 to 4 carbon atoms in the alkoxy part; straight-chain or branched halogenoalkyl with 1 to 4 carbon atoms and 1 to 5 halogen atoms (especially fluorine or chlorine atoms); cycloalkyl with 5 to 7 carbon atoms; aryl with 6 or 10 carbon atoms (for example phenyl) which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro; or aralkyl with 6 or 10 carbon atoms in the aryl part and 1 to 4 carbon atoms in the alkyl part (for example benzyl) which optionally carries one or more substituents on the aryl part selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms and nitro.

Surprisingly, the 2-thiazolone-5-carboxylic acid derivatives of the formula (I), which can be used according to the invention, exhibit a better plant growth-regulating activity than succinic acid 2,2-dimethylhydrazide, known from the prior art, and (2-chloroethyl)-trimethylammonium chloride, which is also known, these compounds being compounds of the same type of action which are recognized to possess a good activity. The compounds usable according to the invention thus represent a valuable enrichment of the art.

Compounds of the formula (I) which can be used particularly preferentially are those in which R$^1$ represents hydrogen, methyl, ethyl, n-propyl, iso-propyl, n-butyl, sec.-butyl, tert.-butyl, methoxymethyl or methoxyethyl, or represents methyl or ethyl substituted by pyridinyl, piperidinyl, pyrrolidinyl, piperazinyl, pyrazolidinyl, morpholinyl, thiamorpholinyl, thiazolyl, imidazolyl, 1,2,4-triazolyl or 1,2,3-triazolyl, or represents methyl or ethyl substituted by methylcarbonyl or ethylcarbonyl, or represents methyl or ethyl substituted by phenylcarbonyl, 4-chlorophenylcarbonyl, 4-methylphenylcarbonyl, 2-methylphenylcarbonyl, 4-trifluoromethylphenylcarbonyl, 4-trichloromethylphenylcarbonyl, 4-methoxyphenylcarbonyl, 3-methoxyphenylcarbonyl, 4-methylthienylcarbonyl or 3-nitrophenylcarbonyl, or represents allyl, cyclopentyl, cyclohexyl, phenyl, naphthyl, 2-chlorophenyl, 3-chlorophenyl, 4-chlorophenyl, 4-methylphenyl, 4-trifluoromethylphenyl, 4-trichloromethylphenyl, 4-methoxyphenyl, 4-methylthiophenyl, 3-nitrophenyl, benzyl, 4-chlorobenzyl, 3-chlorobenzyl, 2-chlorobenzyl, 4-methylbenzyl, 4-trifluoromethylbenzyl, 4-trichloromethylbenzyl, 4-methoxybenzyl, 4-methylthiobenzyl or 3-nitrobenzyl, or represents methylamino, ethylamino, n-propylamino, n-butylamino, phenylamino, dimethylamino, diethylamino, di-n-propylamino, phenylmethylamino, piperidinyl, pyrrolidinyl, morpholinyl, thiamorpholinyl or hexahydroazepinyl, R$^2$ represents hydrogen, methyl, ethyl, n-propyl, iso-propyl, n-butyl, isobutyl, sec.-butyl, tert.-butyl, n-pentyl, 2-ethyl-butyl, 2-methylbutyl, n-hexyl, n-heptyl, n-octyl or n-dodecyl, or represents methyl or ethyl substituted by methoxy, ethoxy, isopropoxy, phenoxy, cyano, cyclohexyl or cyclopentyl, or represents cyclopentyl, cyclohexyl, methylcyclohexyl, 3,3,5-trimethylcyclohexyl, benzyl, 4-chlorobenzyl, 2-chlorobenzyl, 4-methylbenzyl, 4-trifluoromethylbenzyl, 4-trichloromethylbenzyl, 4-methoxybenzyl, 4-methylthiobenzyl, 3-nitrobenzyl or β-(2,6-dichlorophenyl)ethyl and R$^3$ represents hydrogen, methyl, ethyl, n-propyl, iso-propyl, n-butyl, sec.-butyl or tert.-butyl, or represents methyl, ethyl, propyl or butyl substituted by methoxy, ethoxy, isopropoxy, propoxy or n-butoxy, or represents chloromethyl, dichloromethyl, trichloromethyl, cyclohexyl, cyclopentyl, phenyl, naphthyl, 4-chlorophenyl, 3-chlorophenyl, 2-chlorophenyl, 4-methylphenyl, 4-trifluoromethylphenyl, 4-methylthiophenyl, 3-nitrophenyl, 4-chlorobenzyl, 4-methylbenzyl, 4-trifluoromethylbenzyl, 4-methoxybenzyl, 4-methylthiobenzyl or 3-nitrobenzyl.

The following may be mentioned specifically as examples of compounds of the formula (I): 3-methyl-4-methyl-2-thiazolone-5-carboxylic acid ethyl ester, 3-benzyl-4-methyl-2-thiazolone-5-carboxylic acid ethyl ester, 4-methyl-2-thiazolone-5-carboxylic acid ethyl ester, 4-methyl-2-thiazolone-5-carboxylic acid isopropyl ester, 4-methyl-2-thiazolone-5-carboxylic acid β-phenyl-ethyl ester, 4-methyl-3-phenyl-2-thiazolone-5-carboxylic acid ethyl ester, 4-methyl-3-phenyl-2-thiazolone-5-carboxylic acid methyl ester, 4-methyl-2-thiazolone-5-carboxylic acid n-dodecyl ester, 3-(2,6-dichlorophenyl)-4-methyl-2-thiazolone-5-carboxylic acid ethyl ester, 4-ethyl-3-phenyl-2-thiazolone-5-carboxylic acid ethyl ester, 4-methyl-2-thiazolone-5-carboxylic acid benzyl ester, 4-methyl-2-thiazolone-5-carboxylic acid n-butyl ester, 4-methyl-2-thiazolone-5-carboxylic acid cyclohexyl ester, 4-methyl-2-thiazolone-5-carboxylic acid methyl ester, 4-trichloromethyl-2-thiazolone-5-carboxylic acid methyl ester, 4-methyl-2-thiazolone-5-carboxylic acid cyclohexylmethyl ester, 4-methyl-2-thiazolone-5-carboxylic acid β-ethoxy-ethyl ester, 4-methyl-2-thiazolone-5-carboxylic acid β-isopropoxy-ethyl ester, 4-methyl-2-thiazolone-5-carboxylic acid sec,-butyl ester, 4-methyl-2-thiazolone-5-carboxylic acid n-hexyl ester, 4-methyl-2-thiazolone-5-carboxylic acid β-cyano-ethyl ester, 4-methyl-2-thiazolone-5-carboxylic acid n-decyl ester, 4-methyl-2-thiazolone-5-carboxylic acid β-phenoxy-ethyl ester, 3-methyl-4-methyl-2-thiazolone-5-carboxylic acid cyclohexyl ester, 3-phenyl-4-methyl-2-thiazolone-5-carboxylic acid cyclohexyl ester, 3-cyclohexyl-4-methyl-2-thiazolone-5-carboxylic acid ethyl ester, 3-cyclopentyl-4-methyl-2-thiazolone-5-carboxylic acid ethyl ester, 4-methyl-3-(2-methylphenyl)-2-thiazolone-5-carboxylic acid ethyl ester, 4-methyl-3-naphthyl-2-thiazolone-5-carboxylic acid methyl ester, 4-methyl-2-thiazolone-5-carboxylic acid β-2,6-dichlorophenylethyl ester, 4-phenyl-2-thiazolone-5-carboxylic acid methyl ester, 4-naphthyl-2-thiazolone-5-carboxylic acid ethyl ester, 3-methyl-4-(2,6-dichlorophenyl)-2-thiazolone-5-carboxylic acid ethyl ester, 3-methyl-4-naphthyl-2-thiazolone-5-carboxylic acid ethyl ester, 3-methyl-2-thiazolone-5-carboxylic acid ethyl ester, 4-hexyl-3-methyl-2-thiazolone-5-carboxylic acid ethyl ester, 3-hexyl-4-methyl-2-thiazolone-5-carboxylic acid ethyl ester, 4-methyl-2-thiazolone-5-carboxylic acid octadecyl ester, 3-methylamino-4-methyl-2-thiazolone-5-carboxylic acid ethyl ester, 3-ethylamino-4-methyl-2-thiazolone-5-carboxylic acid ethyl ester, 3-n-propylamino-4-methyl-2-thiazolone-5-carboxylic acid ethyl ester, 3-isopropylamino-4-methyl-2-thiazolone-5-carboxylic acid ethyl ester, 3-phenylamino-4-methyl-2-thiazolone-5-carboxylic acid ethyl ester, 3-dimethylamino-4-methyl-2-thiazolone-5-carboxylic acid ethyl ester, 3-diethylamino-4-methyl-2-thiazolone-5-carboxylic acid ethyl ester, 3-(phenylmethyl-amino)-4-methyl-2-thiazolone-5-carboxylic acid ethyl ester and 3-ethyl-4-methyl-2-thiazolone-5-carboxylic acid.

The 2-thiazolone-5-carboxylic acid derivatives of the formula (I), which can be used according to the invention, are in a number of cases known (see Proc. Indian Akad. Sci. 22A, 362–378 (1945), J. Pharm. Soc. Japan 76, 301–305 (1956), DT-OS (German Published Specification) No. 2,137,649 and DT-OS (German Published Specification) No. 2,253,027). Some of the active compounds which can be used according to the invention have not been described in the literature but can be prepared in a simple manner in accordance with processes known in principle.

Thus, compounds of the formula (I) are obtained when (a) β-aminoacrylic acid esters of the general formula

in which $R^1$ and $R^3$ have the above-mentioned meanings and $R^6$ represents the same radicals as $R^2$, with the exception of hydrogen, are reacted with chlorocarbonylsulphenyl chloride of the formula

if appropriate in the presence of an inert diluent, such as chlorobenzene, and, if appropriate, in the presence of an acid-binding agent, such as pyridine, at temperatures between 0° and 200° C., or when (b) 2-thiazolone-5-carboxylic acid esters of the general formula

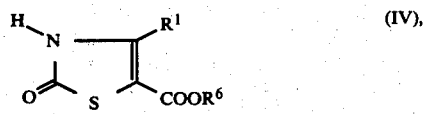

in which $R^1$ and $R^6$ have the above-mentioned meanings, are reacted with halogen compounds of the general formula

in which $R^7$ represents alkyl, alkenyl, cycloalkyl or aralkyl which is optionally substituted in the aryl part and X represents chlorine, bromine or iodine, in the presence of an inert organic solvent, such as acetonitrile, dioxan or toluene, and in the presence of an acid-binding agent, such as triethylamine or pyridine, at temperatures between 60° C. and 160° C., preferably between 70° C. and 120° C., or when (c) 2-thiazolone-5-carboxylic acid esters of the general formula

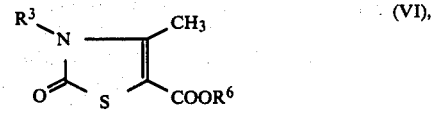

in which $R^3$ and $R^6$ have the above-mentioned meanings, are reacted with elementary chlorine in the presence of a solvent, such as chloroform, carbon tetrachloride or sulphuryl chloride, at temperatures between 20° C. and 120° C., preferably 60° C. and 80° C.

Those compounds of the formula (I) in which $R^2$ represents hydrogen are obtained when esters of the general formula

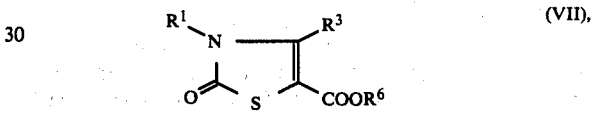

in which $R^1$, $R^3$ and $R^6$ have the above-mentioned meanings, are saponified with the aid of bases, such as sodium hydroxide or potassium hydroxide, in the presence of a solvent, such as an alcohol/water mixture, at temperatures between 0° C. and 100° C., and the mixture is then acidified.

The β-aminoacrylic acid esters required as starting compounds are known or can be prepared in accordance with processes known in principle (see DT-OS (German Published Specification) No. 2,137,649 and DT-OS (German Published Specification) No. 2,253,027).

The compounds of the formula (V), also required as reactants, and chlorocarbonylsulphenyl chloride of the formula (III), are also known or can be prepared in accordance with processes known in principle (see Synthesis 1970, 567).

The active compounds which can be used according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and ULV-formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as a mixture with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming and gassing. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The active compound concentrations can be varied within a substantial range. In general 0.01 to 50 kg, preferably 0.05 to 10 kg, of active compound are employed per hectare of soil surface.

The substances of the formula (I) which can be used according to the invention not only have very good plant growth-regulating properties but in addition also possess a fungicidal activity.

The examples which follow show the activity of the compounds according to the invention as growth regulators without excluding the possibility of further applications as growth regulators.

In these Examples, the compounds according to the present invention are each identified by the number (given in brackets) of the corresponding preparative Example, which will be found later in this specification.

The known comparison compounds are identified as follows:

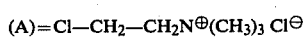

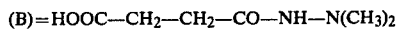

EXAMPLE A

Stimulation of ethylene biosynthesis

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. A constant number of pieces of leaf were incubated for 1 hour in Petri dishes which were filled with 10 ml of the active compound preparations or with corresponding control solutions without active compounds. Thereafter, the pieces of leaf were introduced into vessels which were closed air-tight. A part of the active compound preparations was also introduced into these vessels. After 24 hours the ethylene which had collected in the vessels was determined by customary methods of detection. The evolution of ethylene from the pieces of leaf treated with the active compound preparations was compared with the evolution of ethylene of the controls.

The plant hormone ethylene affects numerous processes during the development of the plants. An increase in ethylene biosynthesis, such as can be achieved with the substances according to the invention, makes it possible to control these processes. The following may be mentioned here as examples in which there is, in particular, commercial interest: detachment of fruit, acceleration of ripening of fruit and leaves, induction of flowering, germination of seeds, thinning-out of fruit, stimulation of latex flux, for example in hevea, and inhibition of growth, for example to prevent the lodging of cereals.

The active compounds (12), (2), (15), (34), (37), (38), (33), (39), (40), (42), (43), (11) and (35) were found to increase ethylene biosynthesis in comparison to the control.

EXAMPLE B

Acceleration of ripening of tomatoes

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Tomato plants were grown out of doors in the usual manner, until half the fruits had colored. At this stage, the plants were sprayed with the active compound preparations until dripping wet. After 2 weeks, the coloring of the fruits was rated in comparison to that of untreated control plants and was designated in terms of a scale of 0 to 3, as follows:

0=no acceleration of ripening (like the untreated control)
1=slight acceleration of ripening
2=moderate acceleration of ripening
3=strong acceleration of ripening The active compounds, active compound concentrations and results can be seen from the table which follows:

TABLE B

| | Acceleration of ripening of tomatoes | |
|---|---|---|
| Active compound | Active compound concentration in % | Acceleration of ripening |
| — (control) | — | 0 |
| (38) | 0.2 | 2 |

EXAMPLE C

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured and the inhibition of growth was calculated in percent of the additional growth of the control plants. 100% meant that growth had stopped, and 0% meant a growth corresponding to that of the control plants.

The active compounds, active compound concentrations and results can be seen from the table which follows.

TABLE C

| | Inhibition of growth of soya beans | |
|---|---|---|
| Active compound | Active compound concentration in % | Inhibition of growth in % |
| — (control) | — | 0 |
| (A) | 0.05 | 0 |
| (12) | 0.05 | 35 |
| (15) | 0.05 | 35 |
| (40) | 0.05 | 25 |
| (43) | 0.05 | 25 |

EXAMPLE D

Inhibition of growth of great maple trees (Acer pseudoplatanus)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

One year old seedlings which had grown to a height of 25 cm were sprayed with the active compound preparations until dripping wet. After 6 weeks' growth in a greenhouse, the additional growth was measured and the inhibition of growth was calculated in percent of the additional growth of the control plants. 100% meant that the growth had stopped and 0% meant a growth corresponding to that of the control plants.

The active compounds, active compound concentrations and results can be seen from the table which follows.

TABLE D

| | Inhibition of growth of great maple trees (*Acer pseudoplatanus*) | |
|---|---|---|
| Active compound | Active compound concentration in % | Inhibition of growth in % |
| — (control) | — | 0 |
| (B) | 1.0 | 20 |
| (15) | 0.4 | 45 |

EXAMPLE E

Promotion of growth of wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Wheat plants in the 2-leaf stage were sprayed with the active compound preparations until dripping wet. After 3 weeks' growth in a greenhouse, the additional growth was measured and the promotion of growth was calculated in percent of the additional growth of the control plants. 0% meant additional growth corresponding to that of the control plants.

The active compounds, active compound concentrations and results can be seen from the table which follows.

TABLE E

| | Promotion of growth of wheat | |
|---|---|---|
| Active compound | Active compound concentration in % | Promotion of growth in % |
| — (control) | — | 0 |
| (44) | 0.05 | 25 |

EXAMPLE F

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the plants was measured and the inhibition of growth was calculated in percent of the additional growth of the control plants. 100% meant that growth had stopped and 0% meant a growth corresponding to that of the control plants.

The active compounds, active compound concentrations and results can be seen from the table which follows.

TABLE F

| Active compound | Inhibition of growth of cotton | |
|---|---|---|
| | Active compound concentration in % | Inhibition of growth in % |
| — (control) | — | 0 |
| (13) | 0.05 | 45 |
| (15) | 0.05 | 95 |
| (45) | 0.05 | 75 |
| (36) | 0.05 | 35 |

EXAMPLE G

Promotion of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the plants was measured and the promotion of growth was calculated in percent of the additional growth of the control plants. 0% meant additional growth corresponding to that of the control plants.

The active compounds, active compound concentrations and results can be seen from the table which follows.

TABLE G

| Active compound | Promotion of growth of cotton | |
|---|---|---|
| | Active compound concentration in % | Promotion of growth in % |
| — (control) | — | 0 |
| (34) | 0.05 | 25 |

PREPARATIVE EXAMPLES

Example 1

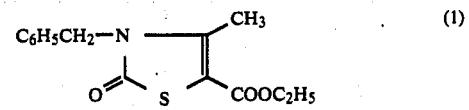

109.5 g (0.5 mole) of β-benzylaminocrotonic acid ethyl ester were added dropwise at 10° C. to 20° C., while cooling with ice, to 72 g (0.55 mole) of chlorocarbonylsulphenyl chloride and 120 ml of dry chlorobenzene. The mixture was then heated to 80° C.–90° C. for about 1 hour, during which vigorous evolution of hydrogen chloride occurred. Lastly, the mixture was heated to the boil until the evolution of gas had ceased, and was filtered hot, and the solvent was stripped off in a waterpump vacuum. The oil which remained was subjected to a fractional high-vacuum distillation. 91 g (66% of theory) of 3-benzyl-4-methyl-2-thiazolone-5-carboxylic acid ethyl ester of boiling point 197°–199° C./0.5 mm Hg were obtained.

Example 2

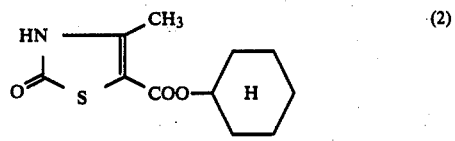

72 g (0.55 mol) of chlorocarbonylsulphenyl chloride were introduced into 100 ml of dry chlorobenzene. 91.5 g (0.5 mol) of β-aminocrotonic acid cyclohexyl ester were added dropwise while cooling with ice and stirring. The mixture was cautiously heated to the boil, during which time the evolution of hydrogen chloride was not allowed to become too vigorous, and was then boiled under reflux until the evolution of gas had ceased. The solvent was distilled off in vacuo and the residue was recrystallized from a small amount of glycol monoethyl ether acetate. 72.5 g (60% of theory) of 4-methyl-2-thiazolone-5-carboxylic acid cyclohexyl ester of melting point 131° C. were obtained.

The following compounds of the general formula

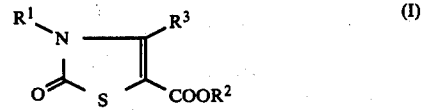

were obtained analogously.

TABLE 1

| Example No. | $R_1$ | $R_2$ | $R_3$ | Melting point (°C.) Boiling point/mm Hg | Yield (% of theory) |
|---|---|---|---|---|---|
| 3 | $CH_3$ | $C_2H_5$ | $CH_3$ | 62–63 | 82 |
| 4 | H | $C_2H_5$ | $CH_3$ | 178 | 75 |
| 5 | H | $(CH_3)_2CH$ | $CH_3$ | 136 | 60 |
| 6 | H | $C_6H_5CH_2CH_2$ | $CH_3$ | 141 | 55 |
| 7 | $C_6H_5$ | $C_2H_5$ | $CH_3$ | 92–94 | 75 |
| 8 | $C_6H_5$ | $CH_3$ | $CH_3$ | 139 | 78 |
| 9 | H | $n\text{-}C_{12}H_{25}$ | $CH_3$ | 94 | 70 |

TABLE 1-continued

| Example No. | R₁ | R₂ | R₃ | Melting point (°C.) Boiling point/mm Hg | Yield (% of theory) |
|---|---|---|---|---|---|
| 10 | 2,6-Cl₂-C₆H₃ | C₂H₅ | CH₃ | 92 | 65 |
| 11 | H | C₆H₅CH₂ | CH₃ | 132 | 45 |
| 12 | H | n-C₄H₉ | CH₃ | 96 | 65 |
| 13 | H | CH₃ | CH₃ | 210 | 58 |
| 14 | H | CH₃ | CCl₃ | 128 | 42 |
| 15 | H | CH₂-C₆H₁₁ | CH₃ | 137 | 85 |
| 16 | H | C₂H₅—O—(CH₂)₂ | CH₃ | 89 | 60 |
| 17 | H | (CH₃)₂CH—O—(CH₂)₂ | CH₃ | 96 | 80 |
| 18 | H | (CH₃)₂CH—CH₂ | CH₃ | 122 | 76 |
| 19 | H | CH₃(CH₂)₅ | CH₃ | 94 | 84 |
| 20 | H | NC—CH₂—CH₂ | CH₃ | 143 | 30 |
| 21 | H | CH₃—(CH₂)₉ | CH₃ | 96 | 88 |
| 22 | H | C₆H₅—O—(CH₂)₂ | CH₃ | 155 | 85 |
| 23 | CH₃ | C₆H₁₁ | CH₃ | 86 | 90 |
| 24 | C₆H₅ | C₆H₁₁ | CH₃ | 135 | 65 |
| 25 | H | CH₃(CH₂)₁₇ | CH₃ | 105 | 80 |
| 26 | H | C₂H₅ | CH₃(CH₂)₁₆ | 42 | 75 |
| 27 | CH₃ | CH₃ | (CH₃)₂CH—O—(CH₂)₂ | 174/0.3 | |
| 28 | CH₃—O—(CH₂)₂ | CH₃ | C₂H₅ | 65 | |
| 29 | C₆H₅ | CH₃ | (CH₃)₂CH—O—(CH₂)₂ | 72 | |
| 30 | H | CH₃ | n-C₄H₉—O—(CH₂)₂ | 70 | |
| 31 | H | CH₃ | n-C₃H₇—O—(CH₂)₂ | 69 | |
| 32 | H | CH₃ | CH₃—CH(OCH₃)—(CH₂)₂ | 84 | |
| 33 | H | (CH₂)₂—CH(CH₃)₂ | CH₃ | 112-113 | |
| 34 | H | CH₂-C₆H₁₁ | CHCl₂ | 165-167 | |
| 35 | H | C₆H₁₁ | —CHCl₂ | 187 | |
| 36 | —N(CH₃)₂ | C₂H₅ | CH₃ | 57 | |
| 37 | H | C₆H₁₁ | —CH₂Cl | 155 | |
| 38 | H | —CH₂—CH(C₂H₅)₂ | —CH₃ | 106 | |
| 39 | H | —(CH₂)₄CH₃ | —CH₃ | 99 | |
| 40 | H | —CH(CH₃)—CH₂—CH(CH₃)₂ | —CH₃ | 89 | |
| 41 | C₆H₁₁—CO—CH₂ | —(CH₂)₁₁—CH₃ | —CH₃ | 83 | |
| 42 | H | 3,3,5-trimethylcyclohexyl | —CH₃ | 134 | |
| 43 | H | 4-methylcyclohexyl | —CH₃ | 97 | |

Example 44

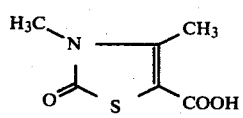

57 g of potassium hydroxide dissolved in 180 ml of water were added to a solution of 201 g (1 mole) of 3,4-dimethyl-2-thiazolone-5-carboxylic acid ethyl ester in 300 ml of ethanol. The mixture was left to stand for 65 hours at room temperature, the alcohol was distilled off in vacuo, the residue was dissolved in water, and the solution was filtered and acidified with half-concentrated hydrochloric acid while cooling with ice. The solid product was filtered off and washed with water and dried.

162.5 g of 3,4-dimethyl-2-thiazolone-5-carboxylic acid of melting point 214° C. were obtained.

EXAMPLE 45

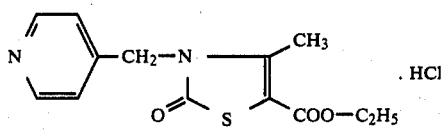

66 g (0.3 mol) of β-(4-pyridylmethylamino)-crotonic acid ethyl ester were added dropwise to a solution of 45 g of chlorocarbonylsulphenyl chloride in 100 ml of dry toluene, while cooling with ice and stirring. The mixture was heated under reflux until the evolution of gas had ceased, the solvent was distilled off in vacuo and the residue was stirred with cold ethanol. The precipitate was filtered off and washed with cold alcohol.

42.9 g of 3-(4-pyridylmethyl)-4-methyl-2-thiazolone-5-carboxylic acid ester hydrochloride of melting point 172°–173° C. were obtained.

It will be understood that the specification and examples are illustrative but not limitative of the present invention and that other embodiments within the spirit and scope of the invention will suggest themselves to those skilled in the art.

What is claimed is:

1. Method for regulating the growth of plants, comprising applying to the plants or their habitat effective amounts of a 2-thiazolone-5-carboxylic acid compound of the formula

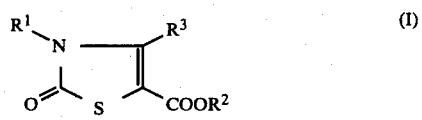

in which
R$^1$ is hydrogen;
alkyl of from 1 to 4 carbon atoms;
alkoxyalkyl of from 1 to 4 carbon atoms in each alkyl moiety;
alkyl of 1 to 4 carbon atoms substituted by phenylcarbonyl
aryl of 6 to 10 carbon atoms optionally substituted with halogen; arylalkyl of 6 to 10 carbon atoms in the aryl moiety and 1 to 4 carbon atoms in the alkyl moiety; or the radical

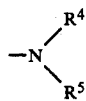

wherein
R$^4$ is straight or branched alkyl of up to 6 carbon atoms and
R$^5$ is straight or branched alkyl of 1 to 6 carbon atoms,
R$^2$ is hydrogen;
alkyl of up to 16 carbon atoms optionally substituted by cycloalkyl of 5 to 7 ring carbon atoms, alkoxy of 1 to 4 carbon atoms, phenoxy, or cyano; cycloalkyl of 5 to 7 ring carbon atoms optionally substituted by alkyl of 1 to 4 carbon atoms; aralkyl of 6 carbon atoms in the aryl moiety and 1 to 4 carbon atoms in the alkyl moiety;
R$^3$ is hydrogen,
alkyl of up to 4 carbon atoms;
alkoxyalkyl of 1 to 4 carbon atoms in each alkyl moiety; haloalkyl of 1 to 4 carbon atoms.

2. Method as claimed in claim 1 wherein R$^1$ is hydrogen.

3. Method as claimed in claim 1 wherein R$^1$ is straight or branched alkyl of 1 to 4 carbon atoms.

4. Method as claimed in claim 1 wherein R$^1$ is straight or branched alkoxyalkyl of 1 to 4 carbon atoms in each alkyl moiety.

5. Method as claimed in claim 1 wherein R$^1$ is straight or branched alkylmercaptoalkyl of from 1 to 4 carbon atoms in each alkyl moiety.

6. Method as claimed in claim 1 wherein R$^1$ is straight or branched alkyl of up to 4 carbon atoms substituted with at least one of saturated and unsaturated heterocyclic radicals of 5 to 7 ring members.

7. Method as claimed in claim 1 wherein R$^1$ is straight or branched alkyl of 1 to 4 carbon atoms substituted by alkylcarbonyl of up to 5 carbon atoms.

8. Method as claimed in claim 1 wherein R$^1$ is straight or branched alkyl of 1 to 4 carbon atoms substituted by phenylcarbonyl or naphthylcarbonyl in which the phenyl or naphthyl radical is optionally substituted with at least one substituent selected independently from halogenalkyl of up to 4 carbon atoms, alkoxy of up to 4 carbon atoms, alkylthio of up to 4 carbon atoms and nitro.

9. Method as claimed in claim 1 wherein R$^1$ is straight or branched alkenyl of 2 to 4 carbon atoms.

10. Method as claimed in claim 1 wherein R$^1$ is cycloalkyl of 5 to 7 ring carbon atoms.

11. Method as claimed in claim 1 wherein R$^1$ is aryl of 6 to 10 carbon atoms optionally substituted with a substituent selected independently from halogenalkyl of up to 4 carbon atoms, haloalkyl of up to 4 carbon atoms, alkoxy of up to 4 carbon atoms, alkylthio of up to 4 carbon atoms and nitro.

12. Method as claimed in claim 1 wherein R$^1$ is arylalkyl of 6 or 10 carbon atoms in the aryl moiety and 1 to 4 carbon atoms in the alkyl moiety optionally substituted in the aryl moiety by at least one substituent selected independently from halogen, alkyl of up to 4 carbon atoms, haloalkyl of up to 4 carbon atoms, alkoxy of up to 4 carbon atoms, alkylthio of up to 4 carbon atoms and nitro.

13. Method as claimed in claim 1 wherein R$^1$ is the

radical wherein
R$^4$ is hydrogen, straight or branched alkyl of up to 6 carbon atoms or aryl of 6 or 10 carbon atoms, and
R$^5$ is straight or branched alkyl of 1 to 6 carbon atoms, alkylcarbonyl of up to 5 carbon atoms, carbalkoxy of up to 5 carbon atoms, alkylsulphonyl of up to 4 carbon atoms or arylsulphonyl of 6 or 10 carbon atoms, or
R$^4$ and R$^5$ together with the nitrogen atom to which they are attached represent a saturated or unsaturated heterocyclic ring of 5 to 7 ring members optionally containing 1 or 2 hetero atoms selected from oxygen, sulfur or —SO$_2$—.

14. Method as claimed in claim 1 wherein $R^2$ is hydrogen.

15. Method as claimed in claim 1 wherein $R^2$ is alkyl of up to 16 carbon atoms optionally substituted by cycloalkyl of 5 to 7 ring carbon atoms, alkoxy of 1 to 4 carbon atoms, alkylmercapto of 1 to 4 carbon atoms, phenoxy, phenylthio or cyano.

16. Method as claimed in claim 1 wherein $R^2$ is cycloalkyl of 5 to 7 ring carbon atoms optionally substituted by alkyl of 1 to 4 carbon atoms.

17. Method as claimed in claim 1 wherein $R^2$ is aralkyl of 6 or 10 carbon atoms in the aryl moiety and 1 to 4 carbon atoms in the alkyl moiety optionally substituted in the aryl moiety by at least one substituent selected independently from halogenalkyl of up to 4 carbon atoms, haloalkyl of up to 4 carbon atoms, alkoxy of up to 4 carbon atoms, alkylthio of up to 4 carbon atoms and nitro.

18. Method as claimed in claim 1 wherein $R^3$ is hydrogen.

19. Method as claimed in claim 1 wherein $R^3$ is straight or branched alkyl of up to 4 carbon atoms.

20. Method as claimed in claim 1 wherein $R^3$ is straight or branched alkoxyalkyl of 1 to 4 carbon atoms in each alkyl moiety.

21. Method as claimed in claim 1 wherein $R^3$ is straight or branched haloalkyl of 1 to 4 carbon atoms.

22. Method as claimed in claim 1 wherein $R^3$ is cycloalkyl of 5 to 7 ring carbon atoms.

23. Method as claimed in claim 1 wherein $R^3$ is aryl of 6 or 10 carbon atoms optionally substituted by at least one substituent selected independently from halogenalkyl of up to 4 carbon atoms, haloakyl of up to 4 carbon atoms, alkoxy of up to 4 carbon atoms, alkylthio of up to 4 carbon atoms and nitro.

24. Method as claimed in claim 1 wherein $R^3$ is aralkyl with 6 or 10 carbon atoms in the aryl moiety and 1 to 4 carbon atoms in the alkyl moiety, optionally substituted in the aryl moiety with at least one substituent selected independently from halogen, alkyl of 1 to 4 carbon atoms, haloalkyl of 1 to 4 carbo atoms, alkoxy of 1 to 4 carbon atoms, alkylthio of 1 to 4 carbon atoms and nitro.

25. Method as claimed in claim 1 wherein said compound is 4-methyl-2-thiazolone-5-carboxylic acid cyclohexyl ester.

26. Method as claimed in claim 1 wherein said compound is 4-methyl-2-thiazolone-5-carboxylic acid n-butyl ester.

27. Method as claimed in claim 1 wherein said compound is 4-methyl-2-thiazolone-5-carboxylic acid cyclohexylmethyl ester.

28. Method as claimed in claim 1 wherein said compound is 4-dichloromethyl-2-thiazolone-5-carboxylic acid cyclohexylmethyl ester.

29. Method as claimed in claim 1 wherein said compound is 4-methyl-2-thiazolone-5-carboxylic acid 3-methylcyclohexyl ester.

30. Method as claimed in claim 1 wherein said compound is applied at a dosage of 0.01 to 50 kg/hectare.

31. Method as claimed in claim 30 wherein said compound is applied at a rate of 0.05 to 10 kg/hectare.

* * * * *